US006720302B2

(12) United States Patent
Frerot et al.

(10) Patent No.: US 6,720,302 B2
(45) Date of Patent: Apr. 13, 2004

(54) METHOD FOR PREPARING A γ-UNSATURATED β-LACTONE AND USE THEREOF AS AN AROMATIC AND FLAVOURING INGREDIENT

(75) Inventors: Eric Frerot, Ville la Grand (FR); Alain Bagnoud, Onex (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 10/044,392

(22) Filed: Jan. 10, 2002

(65) Prior Publication Data

US 2002/0098271 A1 Jul. 25, 2002

Related U.S. Application Data

(63) Continuation of application No. PCT/IB00/00957, filed on Jul. 14, 2000.

(30) Foreign Application Priority Data

Jul. 22, 1999 (CH) ..................................... 1999/1342/99

(51) Int. Cl.$^7$ ................................................. A61K 7/46
(52) U.S. Cl. ............................ 512/25; 512/26; 512/27; 549/263; 549/296; 426/534; 426/650
(58) Field of Search ............................ 512/25, 26, 27; 549/263, 296; 426/534, 650

(56) References Cited

U.S. PATENT DOCUMENTS

| | | | | | |
|---|---|---|---|---|---|
| 3,850,963 | A | * | 11/1974 | Thoma et al. | 549/290 |
| 3,970,673 | A | * | 7/1976 | Banfi | 549/302 |
| 4,113,891 | A | * | 9/1978 | Winter et al. | 426/536 |
| 4,407,740 | A | | 10/1983 | Köpsel et al. | 252/522 |
| 5,464,824 | A | * | 11/1995 | Gaudin | 512/13 |
| 5,679,634 | A | * | 10/1997 | Vial et al. | 512/13 |
| 6,391,365 | B1 | * | 5/2002 | Lambrecht et al. | 426/536 |

FOREIGN PATENT DOCUMENTS

| | | | |
|---|---|---|---|
| CN | 1313402 A | * | 9/2001 |
| EP | 0 953 294 A2 | | 11/1999 |
| JP | 01104187 A | * | 4/1989 |

OTHER PUBLICATIONS

K.H. Schulte–Elte,"Photosensitized oxygenation of Alkyl–Substituted Furans",Tetrahedron, Vol 23, pp. 2583–2599 (1967).
J. A. Hirsch and R.H. Eastman,"The Hydrolysis of α,α'–Dimethoxydihydromenthofuran",*Journal of Organic Chemistry*, vol. 32, No. 9, pp. 2915–2916 (1967).
Woodward et al., "The Autoxidation of Menthofuran", Converse Memorial Lab. of Harvard Univ., pp. 399–403, (1950).
Chi–Keun Shu et al., "Chemical Composition of the Essential Oil of *Pycnanthemum foridanum*", Journal of Essential Oil Research, Vo. 6, No. 5, pp. 529–531 (1994).
K. Umemoto, "Essential Oil of Wind Mints Containing Pulegone and Menthofuran as Major constituents", Laboratory of Chemistry, Nagoya Gakuin University, Vo. 18, No. 2, pp. 79–86 (1981).
T. Nakayama, "A New Japanese Peppermint"Shubi" Developed in Okayama", Department of Food Science and Technology, Kyoto University, No. 97, pp. 46–56, (1970).
Masaaki Ito et al, "Isolation of Menthofurolactone from *Mentha arvensis* and Solvent Effect fo Oil Components on the Fromation", Kitami Kogyp Ta anki Daigaku, Kerkyu Hokoku, Vol 2, No. 4, pp 585–587 (1969).

* cited by examiner

*Primary Examiner*—Jill Warden
*Assistant Examiner*—Monique T. Cole
(74) *Attorney, Agent, or Firm*—Winston & Strawn LLP

(57) ABSTRACT

(6R)-4,5,6,7-Tetrahydro 3,6-dimethyl-3H-benzo[b]furan-2-one is a compound of use in perfumery and the field of flavorings. The compound can be used to impart a minty, slightly vanilla-scented odor, and its flavor imparts sweetness and roundness to the compositions to which it is added.

6 Claims, No Drawings

METHOD FOR PREPARING A γ-UNSATURATED β-LACTONE AND USE THEREOF AS AN AROMATIC AND FLAVOURING INGREDIENT

CROSS-REFERENCE TO RELATED APPLICATIONS

This application is a continuation of the U.S. national stage designation of International application PCT/IB00/00957 filed Jul. 14, 2000 the content of which is expressly incorporated herein by reference thereto.

TECHNICAL FIELD

The present invention relates to the field of perfumery and the flavourings industry. More particularly, it relates to the use of (6R)-4,5,6,7-tetrahydro-3,6-dimethyl-3H-benzo[b]furan-2-one of the formula

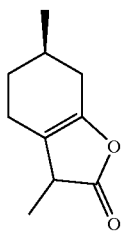

(I)

as a flavouring or perfuming ingredient. The lactone of the formula (I) has excellent organoleptic properties, enabling it to be used to great advantage in perfumery and the flavourings industry.

The present invention also relates to a new process for the preparation of the lactone of the formula (I).

PRIOR ART

The chemical structure of (6R)-4,5,6,7-tetrahydro-3,6-dimethyl-3H-benzo[b]furan-2-one is known. In fact, K. Schulte-Elte et al in Tetrahedron (1967), 23(6), 2583–2599 identified the compound of the formula (I) in a mixture of lactones resulting from the photooxidation of menthofuran. Furthermore, J. Hirsch et al in J. Org. Chem. (1967), 32(9), 2915–2916 also identified the lactone (I) from among other end products resulting from the hydrolysis of α,α'-dimethoxydihydromenthofuran. However, these authors specify that the lactone (I) oxidises very easily under the synthesis conditions described to give a hydroxylactone, 5,6,7,7a-tetrahydro-7a-hydroxy-3,6-dimethyl-4H-benzo[b]furan-2-one of the formula

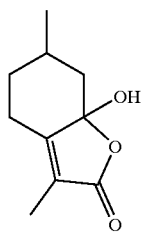

(II)

Moreover, some authors such as R. Woodward et al in J. Am. Chem. Soc. (1950), 72, 399–403, who have studied the oxidation of menthofuran by employing greatly varying experimental conditions, have never identified the lactone (I), but have obtained the hydroxylactone (II) as the only oxidation product.

So, although (6R)-4,5,6,7-tetrahydro-3,6-dimethyl-3H-benzo[b]furan-2-one has been detected among other reaction products during the course of studies into the reactivity of menthofuran, no document of the prior art describes optimum synthesis enabling the lactone (I) to be obtained without it oxidising rapidly to form the hydroxylactone (II). In addition, these references give no indication or even a suggestion of the possible use of the lactone (I) as a perfuming or flavouring ingredient.

Moreover, it is important to point out that certain documents of the prior art, which have analysed the constituents of natural products such as the essential oil *Pycnanthemum floridanum* (C. Shu et al, J. Ess. Oil Res. (1994), 6(5), 529–531) or wild species of peppermint (Nakayama T.; Higashiyama T.; Sakata I.; Hashizume T., Koryo, (1970), 97, 47–56) have identified a product that they refer to as "menthofurolactone", without specifying its structure. It seems that there is some confusion in the literature with respect to the structure associated with this name: while Chemical Abstracts uses menthofurolactone to refer to the structure (6R)-4,5,6,7-tetrahydro-3,6-dimethyl-3H-benzo[b]furan-2-one, i.e. the lactone (I), documents of the prior art use this name to designate 5,6,7,7a-tetrahydro-7a-hydroxy-3,6-dimethyl-4H-benzo[b]furan-2-one of the formula (II).

For example, Ito et al in Kitami Kogyo Tanki Daigaku, Kenkyu Hokoku (1969), 2(4), 585–587, who describe "the isolation of menthofurolactone from *Mentha arvensis*", associate the structure (II) with the name "menthofurolactone" and also describe its synthesis by the oxidation of menthofuran. Without doubt, the confusion arises from the fact that, as mentioned hereinabove, both the lactone (I) and the hydroxylactone (II) are products of the oxidation of menthofuran and, according to the prior art, the lactone (I) oxidises very easily to form the hydroxylactone (II). Consequently, the documents of the prior art by C. Shu et al and K. Umemoto, which refer to menthofurolactone as a constituent of a natural product without describing its structure and which date from later than the document by Ito et al referred to hereinabove, do not make it possible to establish what the structure of the lactone detected and named "menthofurolactone" was. On the basis of the experimental conditions employed in the prior art, the compound detected in the natural products is in fact the hydroxylactone of the formula (II). However, we have discovered quite surprisingly that the lactone of the formula (I) is present in the concrete of peppermint in trace form, although this constituent is very difficult to detect. In particular, we were able to ascertain that only certain experimental conditions, with respect to the choice of GC capillary column, allow the detection of the product by gas chromatography coupled with mass spectrometry, GCMS. For example, during GCMS analysis carried out using a polar column of the type used in the documents of the prior art which disclose analyses of natural products, the lactone (I) is not detected. In contrast, the same GCMS analysis carried out over an apolar column enabled us to observe the presence of (6R)-4,5,6,7-tetrahydro-3,6-dimethyl-3H-benzo[b]furan-2-one. It is clearly apparent from this comparison that the two documents referred to hereinabove are using the name "menthofuro-lactone" to designate the hydroxylactone (II).

Therefore, although of known structure, no document of the prior art describes an optimum synthesis of the lactone (I) which would prevent its rapid oxidation into hydroxylactone (II). Moreover, it seems that this lactone has never been identified as a constituent of a natural product. Finally, there is no mention or suggestion in the prior art of the use of (6R)-4,5,6,7-tetrahydro-3,6-dimethyl-3H-benzo[b]furan-2-one as a perfuming or flavouring ingredient.

DESCRIPTION OF THE INVENTION

We have now discovered quite surprisingly that the lactone of the formula (I) has excellent organoleptic properties, enabling it to be used to great advantage in perfumery and the flavourings industry.

Thus the present invention relates to the use of (6R)-4,5,6,7-tetrahydro-3,6-dimethyl-3H-benzo[b]furan-2-one as a perfuming or flavouring ingredient.

(6R)-4,5,6,7-Tetrahydro-3,6-dimethyl-3H-benzo[b]furan-2-one has a minty, slightly vanilla-scented odour, the flavor of which imparts sweetness and roundness to the compositions to which it is added and produces very pronounced and typical organoleptic effects when the said compound is incorporated into a perfume or flavour, even when greatly diluted.

More particularly, the lactone (I) develops a phenolic/coumarin-like odour, making it a useful alternative to coumarin. (6R)-4,5,6,7-Tetrahydro-3,6-dimethyl-3H-benzo[b]furan-2-one also has a completely original, minty odoriferous note much appreciated by perfumers. In fact, this combination of odoriferous features allows different olfactory nuances to be imparted which, in principle, one would only have been able to obtain with the contribution of a plurality of compounds, the combination of which would, however, produce unavoidably different olfactory effects.

Furthermore, the odour of the compound according to the invention is advantageously powerful.

The lactone of the formula (I) lends itself just as well to use in fine perfumery, in perfumes, eaux de toilette or aftershaves, as to other uses common in perfumery, such as the perfuming of soaps, shower or bath gels, hygiene products or hair care products such as shampoos and conditioners, as well as deodorants, air fresheners and also cosmetic preparations.

(6R)-4,5,6,7-Tetrahydro-3,6-dimethyl-3H-benzo[b]furan-2-one can also be used in applications such as liquid or solid detergents for the treatment of textiles, in fabric softeners and also in detergent compositions or cleaning products for washing up or for cleaning various surfaces in domestic and industrial environments.

In these applications, the compound according to the invention can be used alone or mixed with other perfuming ingredients, solvents or additives commonly used in perfumery. The nature and variety of these co-ingredients do not require further description here, which in any case could not be exhaustive, the skilled person being able to select them on the basis of his general knowledge and according to the nature of the product to be perfumed and the desired olfactory effect. These perfuming co-ingredients can belong to chemical classes as varied as alcohols, aldehydes, ketones, esters, ethers, acetates, nitriles, terpene hydrocarbons and nitrogenous or sulfurous heterocyclic compounds, and also essential oils of natural or synthetic origin. A lot of these ingredients are listed in reference texts such as the book by S. Arctander, Perfume and Flavor Chemicals, 1969, Montclair, N.J., USA, or its more recent versions, and in other works of a similar nature.

The proportions in which the compound according to the invention can be incorporated into the various aforementioned products vary within a very wide range of values. These values depend on the nature of the article or product that one wishes to perfume and on the desired olfactory effect, as well as the nature of the co-ingredients in a given composition when the compound according to the invention is mixed with perfuming co-ingredients, solvents or additives commonly used in the art.

As an example, typical concentrations are in the order of 1% to 10% by weight, even 20% by weight of the compound according to the invention, based on the weight of perfuming composition into which it is incorporated. Lower concentrations can be used when this compound is applied directly in the perfuming of the various consumables mentioned hereinabove.

The compound according to the invention has also proved highly useful in the field of flavourings.

Its taste is typically associated with the characteristic flavours of vanilla or chocolate. The lactone according to the invention imparts a sweetness and a roundness, much appreciated by flavourists, to the compositions to which it is added.

Owing to its characteristics, (6R)-4,5,6,7-tetrahydro-3,6-dimethyl-3H-benzo [b]furan-2-one lends itself particularly well to applications in the field of flavourings where a sugary taste is desired, for example in desserts, sweets and other items of confectionery, compotes, yoghurts and other dairy products, chewing gums and jams. The lactone (I) also lends itself to use in drinks, ice-cream products, cigarettes, chewing tobacco, pharmaceutical preparations and dental care products.

In these applications, the compound according to the invention is typically used in concentrations in the order of 1 ppb to 100 ppm, preferably 10 ppb to 20 ppm, relative to the foodstuffs into which it is incorporated. Higher concentrations can be used when the compound according to the invention is used in the concentrated flavours or flavouring compositions to be incorporated into the consumables.

The invention also relates to a new process for the preparation of (6R)-4,5,6,7-tetrahydro-3,6-dimethyl-3H-benzo[b]furan-2-one. As mentioned herein above, the prior art does not provide an optimum solution to the problem of the synthesis of the lactone (I), which is likely to oxidise into the corresponding hydroxylactone when prepared under the conditions described in the prior art. The present invention provides a solution to the stated problem and thus relates to a process for the preparation of (6R)-4,5,6,7-tetrahydro-3,6-dimethyl-3H-benzo[b]furan-2-one, characterized in that enzymatic oxidation of menthofuran is carried out. In particular, the use of a lipase of the NOVOZYM 435®type, under reaction conditions to be described in greater detail in Example 1 hereinbelow, enables the lactone (I) to be obtained during an oxidation reaction carried out in a controlled manner so as to limit the formation of the hydroxylactone (II).

The invention will now be described in further detail by way of the following examples, in which the temperatures are given in degrees Celsius and the abbreviations have the usual meaning in the art.

Methods of Carrying Out the Invention

EXAMPLE 1

Preparation of (6R)-4,5,6,7-tetrahydro-3,6-dimethyl-3H-benzo[b]furan-2-one 150 g (1 mole) of (R)-(+)-menthofuran (synthetic origin: Toyotama Perf., $[\alpha]^D_{20}$=84.1°; or natural origin: Todd $[\alpha]^D_{20}$=88.1°), 144 g (1 mole) of octanoic acid and 7 g (11,500 U/g, 80,500 units) of immobilised lipase NOVOZYM 435 were diluted in 150 ml of toluene. 142 ml (1.46 moles) of hydrogen peroxide at 35% were then added dropwise to the reaction mixture at 45° over a period of 15 mins. An exothermic reaction was observed. The reaction mixture was then held at ambient temperature for 8 h. After filtration, 600 ml of diethylether were added, then the organic phase was washed successively with Na2CO3 at 5%, brine, water and brine again. 148.3 g of a yellow oil were obtained. After distillation under vacuum over 1 g of 2,6-di-tert-butyl-4-methylphenol (BHT), 37.2 g of (6R)-4,5,6,7-tetrahydro-3,6-dimethyl-3H-benzo[b]furan-2-one were obtained in the form of a mixture of 2 diastereoisomers in a ratio of approximately 1:1, pure to 95% starting from synthetic menthofuran and pure to 85% starting from natural menthofuran, with a yield of 22%.

Analytical data:

$[\alpha]_D 20$ (c=1, EtOH)=+70° (ex Todd) and +75° (ex Toyotama)

B. pt.: 48°–50° (6 Pa)

NMR($^1$H, CDCl$_3$):3.08(m, 1H); 2.33(m, 1H); 2.07(m, 2H); 1.89(m, 2H); 1.79(m, 1H); 1.37(m, 1H); 1.30 and 1.29(2d, J=7.9 and 7.5Hz, 3H, 2 diastereoisomers in a ratio of 1/1); 1.06(d, J=6.3Hz, 3H).

NMR($^{13}$C, CDCl$_3$):180.6 and 180.5(2s, 2 diast.); 148.4(s); 115.3(s); 41.1 and 40.7(d); 30.6 and 30.4(t); 30.13 and 30.08(t); 29.16 and 29.11(d); 21.3(q); 20.7 and 20.5(t); 14.2(q).

MS(EI): 166(100), 151(5), 138(26), 123(39), 110(30), 95(60), 81(85), 67(26), 55(13).

EXAMPLE 2
Preparation of Vanilla Flavour Pudding

A basic pudding mixture was prepared from the following ingredients using conventional methods:

| Ingredients | % by weight |
|---|---|
| Full-cream milk | 81.26 |
| Cream containing 35% fat | 4.50 |
| Powdered skimmed milk | 1.80 |
| Modified maize starch (Clearam CH 20)[1] | 2.00 |
| Sugar | 10.00 |
| Satiagum ADC 25[2] | 0.40 |
| Salt | 0.04 |
| Total | 100.00 |

[1]origin: Roquette Frères, Lille, France
[2]carrageenan; origin: S.B.I., Boulogne Billancourt, France 0.03% vanilla flavour of the following formula was then added:

| Ingredients | % by weight |
|---|---|
| Acetylmethylcarbinol | 5 |
| Anisic aldehyde at 10%* | 5 |
| Diacetyl | 3 |
| Vanillin | 50 |
| Natural vanilla extract | 500 |
| Ethyl alcohol | 437 |
| Total | 1000 |

*in ethanol

This vanilla flavour was evaluated in the pudding preparation, then compared blind, by flavourists, with an identical flavouring to which 0.005% (6R)-4,5,6,7-tetrahydro-3,6-dimethyl-3H-benzo[b]furan-2-one had been added and which was likewise mixed into the pudding preparation in a proportion of 0.03%.

In the opinion of the flavourists, the flavour containing (6R)-4,5,6,7-tetrahydro-3,6-dimethyl-3H-benzo[b]furan-2-one had a sweeter, more rounded tonality than the control flavour.

EXAMPLE 3
Preparation of Chocolate Flavour Pudding

A basic pudding mixture was prepared from the following ingredients using conventional methods:

| Ingredients | % by weight |
|---|---|
| Full-cream milk | 78.94 |
| Cream containing 35% fat | 3.00 |
| Powdered skimmed milk | 1.70 |
| Modified maize starch (Clearam CH 20)[1] | 1.70 |
| Sugar | 11.50 |
| Cocoa: type Zaan D11CM (10%–12% fat)[2] | 1.80 |
| Plain chocolate | 1.00 |
| Satiagum ADC 25[3] | 0.32 |
| Salt | 0.04 |
| Total | 100.00 |

[1]origin: Roquette Frères, Lille, France
[2]origin: Cocoafabrik de Zaan B.V., Koogan de Zaan, Netherlands
[3]carrageenan; origin: Sanofi Bio-Ind., Grasse, France 0.03% chocolate flavour of the following formula was then added:

| Ingredients | % by weight |
|---|---|
| Natural cocoa extract | 560 |
| Natural vanilla extract | 100 |
| Carob extract | 125 |
| Furaneol ®[1] at 10%* | 3 |
| Vanillin | 20 |
| Ethyl alcohol | 192 |
| Total | 1000 |

*in ethanol
[1]4-hydroxy-2,5-dimethyl-3(2H)-furanone; origin: Firmenich SA, Geneva, Switzerland This chocolate flavour was evaluated in the pudding preparation, then compared blind, by flavourists, with an identical flavouring to which 0.005% (6R)-4, 5,6,7-tetrahydro-3,6-dimethyl-3H-benzo[b]furan-2-one had been added and which was likewise mixed into the pudding preparation in a proportion of 0.03%.

In the opinion of the flavourists, the flavouring containing (6R)-4,5,6,7-tetrahydro-3,6-dimethyl-3H-benzo[b]furan-2-one had a sweeter, more rounded tonality than the control flavour, as in Example 2.

EXAMPLE 4
Preparation of Chewing Gum

Chewing gum was prepared from the following ingredients:

| Ingredients | % by weight |
|---|---|
| Base: type Cafosa Dorada Plus T205-01[1] | 18.00 |
| Sugar (particle size: 50 microns) | 61.50 |
| Glucose | 20.00 |
| Glycerin at 85% | 0.50 |
| Total | 100.00 |

Oil of *Mentha arvensis* in a proportion of 1% was evaluated in this chewing gum base. 0.06% (6R)-4,5,6,7-tetrahydro-3,6-dimethyl-3H-benzo[b]furan-2-one was added to this mint oil, which was added in a proportion of 1% to the same chewing gum base. A blind evaluation by a panel of experts showed that the sample containing (6R)-4,5,6,7-tetrahydro-3,6-dimethyl-3H-benzo[b]furan-2-one advantageously had a sweeter, more herbal note reminiscent of peppermint.

1) origin: Cafosa Gum Products Technology, Barcelona, Spain

EXAMPLE 5
Preparation of a Perfuming Composition for an Eau De Toilette

A base composition was prepared from the following ingredients:

| Ingredients | Parts by weight |
| --- | --- |
| Styrallyl acetate | 80 |
| Aldehyde C12 at 50%* | 20 |
| Hexylcinnamic aldehyde | 190 |
| Aldehyde MNA at 10%* | 80 |
| Allyl amyl glycolate at 10%* | 60 |
| Aspic oil | 50 |
| Citronellol | 370 |
| Allyl cyclohexylpropionate | 10 |
| Dihydromyrcenol | 300 |
| Geraniol | 120 |
| Geranyl nitrile | 20 |
| Habanolide ®[1] | 80 |
| Hedione ®[2] | 200 |
| Linalol | 400 |
| γ-Nonalactone at 10%* | 20 |
| Petitgrain oil | 200 |
| Phenethylol | 350 |
| Orange oil | 120 |
| cis-3-Hexenyl salicylate | 30 |
| Terpineol | 50 |
| Triplal ®[3] at 10%* | 20 |
| Vert de Lilas[4] | 30 |
| Total | 2800 |

*in dipropylene glycol
[1] pentadecenolide; origin: Firmenich SA, Geneva, Switzerland
[2] methyl dihydrojasmonate; origin: Firmenich SA, Geneva, Switzerland
[3] 2,4-dimethyl-3-cyclohexen-1-carboxaldehyde; origin: International Flavors & Fragrances, USA
[4] (2,2-dimethoxyethyl)benzene; origin: Firmenich SA, Geneva, Switzerland The addition of 200 parts by weight of (6R)-4,5,6,7-tetrahydro-3,6-dimethyl-3H-benzo[b]furan-2-one to this composition imparts to its odour a powdery, coumarin-like connotation, further accompanied by a fine herbaceous freshness.

EXAMPLE 6
Preparation of a Perfuming Composition

A base composition with floral/heliotropic (sunflower) notes was prepared from the following ingredients:

| Ingredients | Parts by weight |
| --- | --- |
| Cinnamic alcohol at 50%* | 120 |
| Siam benzoin oil at 50%* | 100 |
| Geraniol | 100 |
| Heliotropin | 200 |
| β-Ionone | 30 |
| Muscenone[1] | 50 |
| Phenethylol | 150 |
| α-Terpineol | 60 |
| Ylang oil | 150 |
| Total | 960 |

*in dipropylene glycol
[1] 3-methyl-cyclopentadecenone; origin: Firmenich SA, Geneva, Switzerland 40 parts by weight of (6R)-4,5,6,7-tetrahydro-3,6-dimethyl-3H-benzo[b]furan-2-one are added to 960 parts by weight of this floral/heliotropic composition, imparting to the composition a fine herbaceous, coumarin-like note with an effect of minty freshness. The balsamic note imparted by the heliotropin is intensified, while the cresylic connotation of the ylang oil is well covered by a sweeter note.

What is claimed is:

1. A perfuming or flavoring composition or a perfumed or flavored product containing (6R)-4,5,6,7-tetrahydro-3,6-dimethyl-3H-benzo[b]furan-2-one as perfuming or flavouring ingredient.

2. A product in the form of a perfume or an eau de toilette, soap, shower or bath gel, shampoo or other hair-care product, a cosmetic preparation, a deodorant or air freshener, a detergent or fabric softener or a cleaning product including (6R)-4,5,6,7-tetrahydro-3,6-dimethyl-3H-benzo[b]furan-2-one as perfuming ingredient.

3. A product in the form of a dessert, sweet or other confectionery item, a compote, yoghurt or other dairy product, a chewing gum, jam, drink, ice cream, cigarettes, chewing tobacco, pharmaceutical preparation or dental care product including (6R)-4,5,6,7-tetrahydro-3,6-dimethyl-3H-benzo[b]furan-2-one as a flavoring ingredient.

4. A process for imparting, improving or modifying the roundness and/or sweetness of a flavouring composition or flavoured product, characterised in that (6R)-4,5,6,7-tetrahydro-3,6-dimethyl-3H-benzo[b]furan-2-one is added to the said composition or the said product.

5. A process for the preparation of (6R)-4,5,6,7-tetrahydro-3,6-dimethyl-3H-benzo[b]furan-2-one, characterised in that enzymatic oxidation of (R)-menthofuran is carried out.

6. A process according to claim 5, characterised in that the enzymatic oxidation is carried out in the presence of a lipase of the NOVOZYM 435 ®type.

* * * * *

UNITED STATES PATENT AND TRADEMARK OFFICE
CERTIFICATE OF CORRECTION

PATENT NO. : 6,720,302 B2  
DATED : April 13, 2004  
INVENTOR(S) : Frerot et al.

Page 1 of 1

It is certified that error appears in the above-identified patent and that said Letters Patent is hereby corrected as shown below:

Title page,
Item [30], Foreign Application Priority Data, change "1999/1342/99"
to -- 1342/99 --.
Item [56], References Cited, U.S. PATENT DOCUMENTS, change
"3,970,673 A * 1976 Banfi" to -- 3,970,673 A * 1976 Kondo et al. --.
OTHER PUBLICATIONS:
"K.H. Schulte-Elte" reference, delete "K.H. Schulte-Elte" and insert -- Foote et al. --.
Woodward et al. reference, delete "Converse Memorial Lab. of Harvard Univ.,
pp. 399-403, (1950)" and insert -- J. Am. Chem. Soc., Vol. 72, No. 1, pp. 399-403
(1950) --
K. Umemoto reference, change "Essential Oil of Wind Mints Containing" to
-- Essential Oil of Wild Mints Containing --.
Masaaki Ito et al. reference, change "Isolation of Menthofurolactone from
*Mentha arvensis* and Solvent Effect fo Oil Components on the Fromation",
Kitami Kogyp Ta anki Daigaku, Kerkyu Hokoku, Vol. 2, No. 4, pp. 585-587
 (1969)" to -- Isolation of Menthofurolactone from *Mentha arvensis* and
Solvent Effect of Oil Components on the Formation", Kitami Kogyo Tanki
Daigaku, Kenkyu Hokoku Vol. 2, No. 4, pp. 585-587 (1969) --.

Column 4,
Line 61, change "NOVOZYM 435" to -- NOVOZYM 435® --.

Column 8,
Line 34, change "one as perfuming ingredient" to -- one as a perfuming ingredient --.

Signed and Sealed this

First Day of June, 2004

JON W. DUDAS  
*Acting Director of the United States Patent and Trademark Office*